United States Patent
Cavalla et al.

(10) Patent No.: US 6,228,859 B1
(45) Date of Patent: May 8, 2001

(54) PURINE DERIVATIVES HAVING PHOSPHODIESTERASE IV INHIBITION ACTIVITY

(75) Inventors: David J. Cavalla, Cambridge (GB); Mark Chasin, Manalapan, NJ (US); Peter Hofer, Liestal (CH); Andre Gehrig, Basel (CH); Peter Wintergerst, Basel (CH)

(73) Assignee: Euro-Celtique S.A., Luxembourg (LU)

( * ) Notice: Subject to any disclaimer, the term of this patent is extended or adjusted under 35 U.S.C. 154(b) by 0 days.

(21) Appl. No.: 09/210,556

(22) Filed: Dec. 11, 1998

Related U.S. Application Data
(60) Provisional application No. 60/069,371, filed on Dec. 12, 1997.

(51) Int. Cl.$^7$ .................. C07D 473/34; A61K 31/52; A61P 11/06; A61P 29/00
(52) U.S. Cl. ............................. 514/261; 544/277
(58) Field of Search ............... 514/261; 544/277

(56) References Cited

U.S. PATENT DOCUMENTS

| | | | |
|---|---|---|---|
| Re. 31,429 | 10/1983 | Tull et al. | 544/277 |
| 2,691,654 | 10/1954 | Hitchings | 544/277 |
| 2,697,709 | 12/1954 | Hitchings et al. | 260/252 |
| 2,844,577 | 7/1958 | Acker | 544/277 |
| 2,903,455 | 9/1959 | Strong | 544/277 |
| 2,956,998 | 10/1960 | Baizer | 544/277 |
| 2,957,875 | 10/1960 | Lyttle | 544/277 |
| 2,966,488 | 12/1960 | Shive | 544/277 |
| 3,079,378 | 2/1963 | Schroeder et al. | 260/211.5 |
| 3,135,753 | 6/1964 | Hitchings | 540/265 |
| 3,215,696 | 11/1965 | Denayer | 544/277 |
| 3,225,046 | 12/1965 | Zwahlen | 544/277 |
| 3,669,979 | 6/1972 | Freyermuth | 260/304 |
| 3,952,001 | 4/1976 | Brooks et al. | 260/308 |
| 4,241,063 | 12/1980 | Natio et al. | 424/253 |
| 4,361,699 | 11/1982 | Rasmusson et al. | 544/277 |
| 4,407,802 | 10/1983 | Graham et al. | 424/253 |
| 4,492,592 | 1/1985 | Diaz et al. | 62/18 |
| 4,728,644 | 3/1988 | Yuki et al. | 514/212 |
| 4,883,801 | 11/1989 | Nathanson | 514/263 |
| 4,971,972 | 11/1990 | Doll et al. | 514/265 |
| 4,981,857 | 1/1991 | Daluge et al. | 514/263 |
| 5,057,517 | 10/1991 | Johnston et al. | 514/254 |
| 5,091,431 | 2/1992 | Tulshian et al. | 514/262 |
| 5,110,818 | 5/1992 | Allgeier | 514/261 |
| 5,117,830 | 6/1992 | McAfee | 128/654 |
| 5,177,074 | 1/1993 | Allen et al. | 514/234.2 |
| 5,270,316 | 12/1993 | Suzuki et al. | 514/267 |
| 5,290,782 | 3/1994 | Suzuki et al. | 514/263 |
| 5,939,422 | 8/1999 | Cavalla et al. | 514/261 |

FOREIGN PATENT DOCUMENTS

| | | |
|---|---|---|
| 0203721 | 12/1986 | (EP) . |
| 256692 | 2/1988 | (EP) . |
| 0675124 | 10/1995 | (EP) . |
| 0728759 | 8/1996 | (EP) . |
| 1548252 | 10/1968 | (FR) . |
| 1077689 | 8/1967 | (GB) . |
| 2041359 | 9/1980 | (GB) . |
| 2120065 | 12/1983 | (GB) . |

(List continued on next page.)

OTHER PUBLICATIONS

Isomura, Y, et al., "Studies on the Synthesis and Anti-Inflammatory Activity of 2,6-Di-tert-butylphenols with a Heterocyclic Group at the 4-Position. I." Chem. Pharm. Bull. 31(9) 3168-3178 (1983).

(List continued on next page.)

*Primary Examiner*—Mark L. Berch
(74) *Attorney, Agent, or Firm*—Davidson, Davidson & Kappel, LLC

(57) ABSTRACT

Disclosed are compounds of the formula (I):

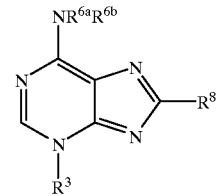

wherein $R^3$ is selected from the group consisting of $C_{1-10}$ alkyl, $C_{1-10}$ alkenyl, $C_{3-10}$ cycloalkyl, $C_{4-10}$ cycloalkylalkyl or $C_{3-10}$ cycloalkenyl, wherein said alkyl, alkenyl, cycloalkyl, cycloalkylalkyl or cycloalkenyl is optionally substituted in one position with hydroxy; or benzyl, wherein said benzyl is optionally substituted in one or two positions with halogen, alkoxy, cycloalkoxy or polycycloalkyl, and wherein said alkyl moiety of said alkoxy or cycloalkoxy substituent is optionally substituted in one position with hydroxy;

$R^8$ is selected from the group consisting of hydrogen, $C_{1-10}$ alkyl, $C_{1-10}$ alkenyl, $C_{3-10}$ cycloalkyl, $C_{4-10}$ cycloalkylalkyl or $C_{3-10}$ cycloalkenyl, wherein said alkyl, alkenyl, cycloalkyl, cycloalkylalkyl or cycloalkenyl is optionally substituted in one position with hydroxy; or benzyl, wherein said benzyl is optionally substituted in one or two positions with halogen, alkoxy, cycloalkoxy or polycycloalkyl, and wherein said alkyl moiety of said alkoxy or cycloalkoxy is optionally substituted in one position with hydroxy;

$R^{6a}$ and $R^{6b}$ are independently selected from the group consisting of hydrogen, $C_{1-10}$ alkyl, $C_{1-10}$ alkenyl, $C_{3-10}$ cycloalkyl, $C_{4-10}$ cycloalkylalkyl, or $C_{3-10}$ cycloalkenyl, wherein said alkyl, alkenyl, cycloalkyl, cycloalkylalkyl or cycloalkenyl is optionally substituted in one position with hydroxy;

and pharmaceutically acceptable salts thereof.

45 Claims, No Drawings

FOREIGN PATENT DOCUMENTS

| | | |
|---|---|---|
| 7606986 | 1/1976 | (JP) . |
| 5121529 | 2/1976 | (JP) . |
| 7654587 | 5/1976 | (JP) . |
| 0215948 | 10/1989 | (NZ) . |
| 8706576 | 11/1987 | (WO) . |
| 9314081 | 7/1993 | (WO) . |
| 9314082 | 7/1993 | (WO) . |
| 9325517 | 12/1993 | (WO) . |
| 9402465 | 2/1994 | (WO) . |
| 9410118 | 5/1994 | (WO) . |
| 9412461 | 6/1994 | (WO) . |
| 9414742 | 7/1994 | (WO) . |
| 9414800 | 7/1994 | (WO) . |
| 9420446 | 9/1994 | (WO) . |
| 9420455 | 9/1994 | (WO) . |
| 9422859 | 10/1994 | (WO) . |
| 95/00516 * | 1/1995 | (WO) . |

OTHER PUBLICATIONS

Ashton, et al., "Selective Type IV Phosphodiesterase Inhibitors as Antiasthmatic Agents. The Synthesis and Biological Activities of 3–(Cyclopentyloxy)–4–methoxybenzamides and Analogues." J. Med. Chem., vol. 37, No. 11 1696–1703 (1994).
K.R.H. Woolridge and R. Slack, "The Synthesis of Some 6–Thioxanthines." Annex IV, 1863–1868 (1962).
Robins, JACS, 74, 1952, 3624.
Stafford and Feldman, "Annual Reports in Medicinal Chemistry", Academic Press, San Diego, 1966, Chapt. 8, pp. 76–78.
Gertrude Elion, JOC, 27, 1962, 2478–2491.
Bergman & Tamari, J. Chem. Soc., 1961, 4468–4472.
Shimade, Junichi, Kuroda, Takeshi, Suzuki, Fumio, J. Heterocycl. Chem., 30(1), 241–6 (English) 1993.
Buell, J. Biol. Chem., 72, 1927, 745.
Suzuki, Fumio, Shimada, Junichi, Ninaka, Ishi, Akio, Shiozaki, Shuzuo, Ichikawa, Shunki, Ono, Eikichi, J. Med. Chem., 35(19), 3578–81 (English) 1992.
Moharra, Hussieny H., Mansour, S.A., Osman, A.N., Egypt. J. Pharm. Sci., 31(1–4), 487–94 (English), (1990).
S.C.J. Fu et al., JOC, 30, 1965, 1916–1920.
Henry Koppel & Roland Robins, JOC, 23, 1958, 1457–1460.
Giner–Sorrolla, Alfred, Segarra, Jay T., Hadden, John W., Nucleic Acid Chem. vol. 4, 10–15, undated.
Girschovich, Chem Abs 116, 173873 (1991).
Montgomery, J.A.C.S. 81, 3963 (1959).
Elion, Chem Abs 53, 6243h (1957).
Fuji, J. Med. Chem. 22, 125 (1979).
Reitz, J. Org. Chem 55, 5761 (1990).
Itaya, Tet. Letters 23, 2203 (1982).
Enoki, Chem Abs 85, 5692 (1976).
Kazimierczuk, Chem Abs 82, 125358 (1974).
Ulbricht, Chem Abs 75, 49027b (1971).
Aida, Chem Abs 86, 43746 (1976).
Enoki, Chem Abs 84, 180299 (1976).
G. T. Rogers et al.: "Synthesis of 3–methylisoguanine '6–Amino–3–methylpurin–2(3H)–One!" Journal of the Chemical Society C, No. 12, 1971, pp. 2364–2366, XP002095992.
Elion, G. "Some new n–methylpurines" CIBA Foundations Symp. Chem. Biol. Purines, 1957, pp 39–49.
Glusenkamp, K, et al., Tautomer–specific anti–(M–3–substituted)–adenine antibodies: new tools in molecular dosimetry & epidemiology, Agnew Chem. Int. Ed. Engl. 1993, 32, No. 11, pp. 1640–1641.
Er–Rhaimini, Tet. Letters 31(40) 5757, 1990.*

* cited by examiner

PURINE DERIVATIVES HAVING PHOSPHODIESTERASE IV INHIBITION ACTIVITY

This application claims priority from U.S. Provisional Patent Application Ser. No. 60/069,371, filed Dec. 12, 1997.

BACKGROUND OF THE INVENTION

Asthma is a complex disease involving the concerted actions of multiple inflammatory and immune cells, spasmogens, inflammatory mediators, cytokines and growth factors. In recent practice there have been four major classes of compounds used in the treatment of asthma, namely bronchodilators (e.g., β-adrenoceptor agonists), anti-inflammatory agents (e.g., corticosteroids), prophylactic anti-allergic agents (e.g., cromolyn sodium) and xanthines (e.g., theophylline) which appear to possess both bronchodilating and anti-inflammatory activity.

Theophylline has been a preferred drug of first choice in the treatment of asthma. Although it has been touted for its direct bronchodilatory action, theophylline's therapeutic value is now believed to also stem from anti-inflammatory activity. Its mechanism of action remains unclear. However, it is believed that several of its cellular activities are important in its activity as an anti-asthmatic, including cyclic nucleotide phosphodiesterase inhibition, adenosine receptor antagonism, stimulation of catecholamine release, and its ability to increase the number and activity of suppressor T-lymphocytes. While all of these may actually contribute to its activity, only PDE inhibition may account for both the anti-inflammatory and bronchodilatory components. However, theophylline is known to have a narrow therapeutic index and a wide range of untoward side effects which are considered problematic.

Of the activities mentioned above, theophylline's activity in inhibiting cyclic nucleotide phosphodiesterase has received considerable attention recently. Cyclic nucleotide phosphodiesterases (PDEs) have received considerable attention as molecular targets for anti-asthmatic agents. Cyclic 3',5'-adenosine monophosphate (cAMP) and cyclic 3',5'-guanosine monophosphate (cGMP) are known second messengers that mediate the functional responses of cells to a multitude of hormones, neurotransmitters and autocoids. At least two therapeutically important effects could result from phosphodiesterase inhibition, and the consequent rise in intracellular adenosine 3',5'-monophosphate (cAMP) or guanosine 3',5'-monophosphate (cGMP) in key cells in the pathophysiology of asthma. These are smooth muscle relaxation (resulting in bronchodilation) and anti-inflammatory activity.

It has become known that there are multiple, distinct PDE isoenzymes which differ in their cellular distribution. A variety of inhibitors possessing a marked degree of selectivity for one isoenzyme or the other have been synthesized.

The structure-activity relationships (SAR) of isozyme-selective inhibitors has been discussed in detail, e.g., in the article of Theodore J. Torphy, et al., "Novel Phosphodiesterase Inhibitors For The Therapy Of Asthma", Drug News & Prospectives, 6(4) May 1993, pages 203–214. The PDE enzymes can be grouped into five families according to their specificity toward hydrolysis of cAMP or cGMP, their sensitivity to regulation by calcium, calmodulin or cGMP, and their selective inhibition by various compounds. PDE I is stimulated by $Ca^{2+}$/calmodulin. PDE II is cGMP-stimulated, and is found in the heart and adrenals. PDE III is cGMP-inhibited, and inhibition of this enzyme creates positive inotropic activity. PDE IV is cAMP specific, and its inhibition causes airway relaxation, antiinflammatory and antidepressant activity. PDE V appears to be important in regulating cGMP content in vascular smooth muscle, and therefore PDE V inhibitors may have cardiovascular activity.

While there are compounds derived from numerous structure activity relationship studies which provide PDE III inhibition, the number of structural classes of PDE IV inhibitors is relatively limited. Analogues of rolipram, which has the following structural formula (A):

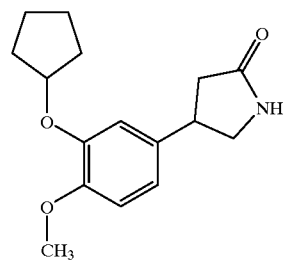

and of RO-20-1724, which has the following structural formula (B):

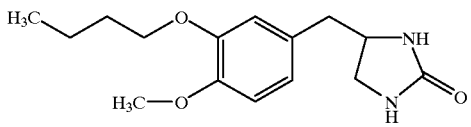

have been studied.

U.S. Pat. No. 4,308,278 discloses compounds of the formula (C)

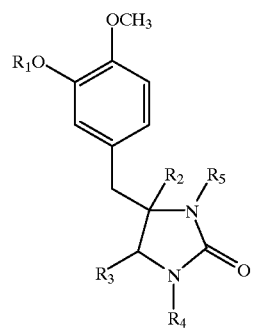

wherein $R_1$ is ($C_3$–$C_6$) cycloalkyl or benzyl; each of $R_2$ and $R_3$ is hydrogen or ($C_1$–$C_4$) alkyl; $R_4$ is $R_2$ or alkoxycarbonyl; and $R_5$ is hydrogen or alkoxycarbonyl.

Compounds of Formula (D) are disclosed in U.S. Pat. No. 3,636,039. These compounds are benzylimidazolidinones which act as hypertensive agents.

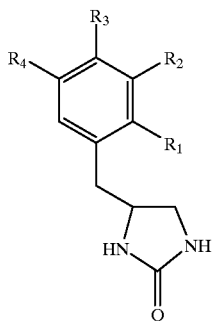

Substituents $R_1$–$R_4$ in Formula D represent a variety of groups, including hydrogen and lower alkyl.

PCT publication WO 87/06576 discloses antidepressants of Formula E:

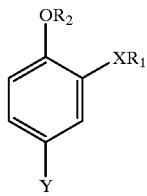

wherein $R_1$ is a polycycloalkyl group having from 7 to 11 carbon atoms; $R_2$ is methyl or ethyl; X is O or NH; and Y comprises a mono-or bicyclic heterocyclic group with optional substituents.

Rolipram, which was initially studied because of its activity as an anti-depressant, has been shown to selectively inhibit the PDE IV enzyme and this compound has since become a standard agent in the classification of PDE enzyme subtypes. There appears to be considerable therapeutic potential for PDE IV inhibitors. Early work focused on depression as a CNS therapeutic endpoint and on inflammation, and has subsequently been extended to include related diseases such as dementia and asthma. In-vitro, rolipram, RO20-1724 and other PDE IV inhibitors have been shown to inhibit (1) mediator synthesis/release in mast cells, basophils, monocytes and eosinophils; (2) respiratory burst, chemotaxis and degranulation in neutrophils and eosinophils; and (3) mitogen-dependent growth and differentiation in lymphocytes (The PDE IV Family Of Calcium-Phosphodiesterases Enzymes, John A. Lowe, III, et al., Drugs of the Future 1992, 17(9):799–807).

PDE IV is present in all the major inflammatory cells in asthma including eosinophils, neutrophils, T-lymphocytes, macrophages and endothelial cells. Its inhibition causes down regulation of inflammatory cell activation and relaxes smooth muscle cells in the trachea and bronchus. On the other hand, inhibition of PDE III, which is present in myocardium, causes an increase in both the force and rate of cardiac contractility. These are undesirable side effects for an anti-inflammatory agent. Theophylline, a non-selective PDE inhibitor, inhibits both PDE III and PDE IV, resulting in both desirable anti-asthmatic effects and undesirable cardiovascular stimulation. With this well-known distinction between PDE isozymes, the opportunity for concomitant anti-inflammation and bronchodilation without many of the side effects associated with theophylline therapy is apparent. The increased incidence of morbidity and mortality due to asthma in many Western countries over the last decade has focused the clinical emphasis on the inflammatory nature of this disease and the benefit of inhaled steroids. Development of an agent that possesses both bronchodilatory and antiinflammatory properties would be most advantageous.

It appears that selective PDE IV inhibitors should be more effective with fewer side effects than theophylline. Clinical support has been shown for this hypothesis. Furthermore, it would be desirable to provide PDE IV inhibitors which are more potent and selective than rolipram and therefore have a lower $IC_{50}$ so as to reduce the amount of the agent required to effect PDE IV inhibition.

In recent years, several different compounds have been suggested as possible therapeutic compositions which achieve the desired PDE IV inhibition without the side effects alluded to above. However, these efforts have been chiefly directed to developing non-specific derivatives of particular classes of compounds, i.e. rolipram analogs, benzoxazoles, adenines, thioxanthines, etc. These efforts, however, have resulted in a myriad of compounds having a wide range of PDE IV $IC_{50}$'s. Often, the general formulas disclosed yield several compounds which have poor levels of PDE IV inhibition and/or lack sufficient specificity. Consequently, these efforts often provide no assurance that any particular derivative within the formula will have the desired combination of high PDE IV inhibition and selectivity.

OBJECTS AND SUMMARY OF THE INVENTION

It is accordingly a primary object of the present invention to provide new compounds which are more effective selective PDE IV inhibitors than known prior art compounds.

It is another object of the present invention to provide new compounds which act as effective PDE IV inhibitors with lower PDE III inhibition.

It is another object of the present invention to provide methods for treating a patient requiring PDE IV inhibition.

It is another object of the present invention to provide new compounds for treating disease states associated with abnormally high physiological levels of inflammatory cytokines, including tumor necrosis factor.

It is another object of the present invention to provide a method of synthesizing the new compounds of this invention.

It is another object of the present invention to provide a method for treating a patient suffering from disease states such as asthma; allergies; inflammation; depression; dementia, including Alzheimer's disease, vascular dementia, and multi-in-farct dementia; a disease caused by Human Immunodeficiency Virus; and disease states associated with abnormally high physiological levels of inflammatory cytokines.

Other objects and advantages of the present invention will become apparent from the following detailed description thereof.

With this and other objects in view, the present invention comprises compounds having the general formula (I):

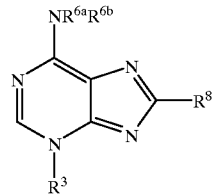

wherein $R^3$ is selected from the group consisting of $C_{1\text{-}10}$ alkyl, $C_{1\text{-}10}$ alkenyl, $C_{3\text{-}10}$ cycloalkyl, $C_{4\text{-}10}$ cycloalkylalkyl or $C_{3-10}$ cycloalkenyl, wherein said alkyl, alkenyl, cycloalkyl, cycloalkylalkyl or cycloalkenyl is optionally substituted in one position with hydroxy; or benzyl, wherein said benzyl is optionally substituted in one or two positions with halogen, alkoxy, cycloalkoxy or polycycloalkyl, and wherein said alkyl moiety of said alkoxy or cycloalkoxy substituent is optionally substituted in one position with hydroxy;

$R^8$ is selected from the group consisting of hydrogen, $C_{1-10}$ alkyl, $C_{1-10}$ alkenyl, $C_{3-10}$ cycloalkyl, $C_{4-10}$ cycloalkylalkyl or $C_{3-10}$ cycloalkenyl, wherein said alkyl, alkenyl, cycloalkyl, cycloalkylalkyl or cycloalkenyl is optionally substituted in one position with hydroxy; or benzyl, wherein said benzyl is optionally substituted in one or two positions with halogen, alkoxy, cycloalkoxy or polycycloalkyl, and wherein said alkyl moiety of said alkoxy or cycloalkoxy is optionally substituted in one position with hydroxy;

$R^{6a}$ and $R^{6b}$ are independently selected from the group consisting of hydrogen, $C_{1-10}$ alkyl, $C_{1-10}$ alkenyl, $C_{3-10}$ cycloalkyl, $C_{4-10}$ cycloalkylalkyl or $C_{3-10}$ cycloalkenyl, wherein said alkyl, alkenyl, cycloalkyl, cycloalkylalkyl or cycloalkenyl is optionally substituted in one position with hydroxy;

and pharmaceutically acceptable salts thereof.

In particular embodiments of the invention, when $R^{6a}$ and $R^{6b}$ are both hydrogen, or when $R^8$ is hydrogen, then $R^3$ is benzyl substituted in two positions with alkoxy, cycloalkoxy, or polycycloalkyl, wherein said alkyl moiety of said alkoxy or cycloalkoxy substituent is optionally substituted in one position with hydroxy.

In certain embodiments of compounds of Formula I, $R^8$ is not hydrogen.

In certain embodiments, $R^{6a}$ and $R^{6b}$ are both hydrogen, or $R^{6a}$ is hydrogen and $R^{6b}$ is a $C_{1-10}$ alkyl, which is optionally substituted with a hydroxyl group. In a still additional embodiment, $R^{6a}$ is hydrogen and $R^{6b}$ is ethyl, which is optionally substituted with a hydroxyl group.

In certain embodiments, $R^3$ is a benzyl substituted with alkoxy and cycloalkoxy, wherein the cycloalkoxy substituent is optionally substituted with a hydroxyl group. In a further embodiment, $R^3$ is substituted with methoxy and cyclopentyloxy, wherein the cyclopentyloxy substituent is optionally substituted with a hydroxyl group. In a still additional embodiment, $^3$ is 3-cyclopentyloxy-4-methoxybenzyl, wherein the cyclopentyl moiety of the cyclopentyloxy is optionally substituted with a hydroxyl group.

In certain additional embodiments, $R^8$ is a $C_{1-10}$ alkyl or $C_{3-10}$ cycloalkyl, optionally substituted with a hydroxyl group. In other embodiments $R^8$ is a $C_{1-10}$ alkyl, optionally substituted with a hydroxyl group. In still additional embodiments, $R^3$ is isopropyl, optionally substituted with a hydroxyl group.

DETAILED DESCRIPTION OF THE INVENTION

As used herein, the following terms are intended to have the meaning as understood by persons of ordinary skill in the art, and are specifically intended to include the meanings set forth below:

As used herein, the term "alkyl" means a linear or branched saturated aliphatic hydrocarbon group having a single radical. Examples of alkyl groups include methyl, propyl, isopropyl, butyl, n-butyl, isobutyl, sec-butyl, tert-butyl, and pentyl. A branched alkyl means that one or more alkyl groups such as methyl, ethyl or propyl, replace one or both hydrogens in a —$CH_2$— group of a linear alkyl chain.

The term "cycloalkyl" means a non-aromatic monocyclic hydrocarbon ring system having a single radical. Exemplary monocyclic cycloalkyl rings include cyclopropyl, cyclopentyl, and cyclohexyl.

The term "polycycloalkyl" means a non-aromatic multi-cyclic hydrocarbon ring system having a single radical. Exemplary polycycloalkyl groups include adamantyl, bornyl and norbornyl.

The term "alkenyl" means a linear or branched aliphatic hydrocarbon group containing a carbon-carbon double bond and having a single radical. A "branched" alkenyl means that one or more alkyl groups such as methyl, ethyl or propyl replace one or both hydrogens in a —$CH_2$— or —CH= linear alkenyl chain. Exemplary alkenyl groups include ethenyl, 1- and 2- propenyl, 1-, 2- and 3- butenyl, 3-methylbut-2-enyl, 2-propenyl, heptenyl, octenyl and decenyl.

The term "cycloalkenyl" means a non-aromatic monocyclic or multicyclic hydrocarbon ring system containing a carbon-carbon double bond and having a single radical. Exemplary monocyclic cycloalkenyl rings include cyclopropenyl, cyclopentenyl, cyclohexenyl or cycloheptenyl. An exemplary multicyclic cycloalkenyl ring is norbornenyl.

The term "cycloaklylalkyl" or "cycloaklyl-alkyl" means a non-aromatic mono- or multicyclic ring system, wherein the ring is substituted with an alkyl group, as defined above to include a linear or branched aliphatic hydrocarbon group having a single radical The term "aralkyl" or "arylalkyl" or "aryl-alkyl" means an alkyl group as defined above to include a linear or branched saturated aliphatic hydrocarbon group having a single radical, wherein the alkyl is substituted with an aryl group, as defined above to include a carbocyclic aromatic ring system containing one, two or three rings which may be attached together in a pendent manner or fused, and containing a single radical.

The term "alkoxy" means an alkyl-O-group in which the alkyl group is as previously defined, to include a linear or branched saturated aliphatic hydrocarbon group having a single radical. Exemplary alkoxy groups include methoxy, ethoxy, n-propoxy, i-propoxy, and n-butoxy.

The term "cycloalkoxy" means a cycloalkyl-O-group in which the cycloalkyl group is as previously defined, to include non-aromatic mono- or multicyclic hydrocarbon ring systems having a single radical. Exemplary cycloalkoxy groups include cyclopentyloxy.

As used herein, the term "patient" includes both human and other mammals.

The present invention also includes organic and inorganic salts, hydrates, esters, prodrugs and metabolites of the compounds of formula I.

The compounds of the present invention can be administered to anyone requiring PDE IV inhibition. Administration may be orally, topically, by suppository, inhalation or insufflation, or parenterally.

The present invention also encompasses all pharmaceutically acceptable salts of the foregoing compounds. One skilled in the art will recognize that acid addition salts of the presently claimed compounds may be prepared by reaction of the compounds with the appropriate acid via a variety of known methods.

Various oral dosage forms can be used, including such solid forms as tablets, gelcaps, capsules, caplets, granules, lozenges and bulk powders and liquid forms such as emulsions, solution and suspensions. The compounds of the present invention can be administered alone or can be combined with various pharmaceutically acceptable carriers and excipients known to those skilled in the art, including but not limited to diluents, suspending agents, solubilizers, binders, disintegrants, preservatives, coloring agents, lubricants and the like.

When the compounds of the present invention are incorporated into oral tablets, such tablets can be compressed, tablet triturates, enteric-coated, sugar-coated, film-coated, multiply compressed or multiply layered. Liquid oral dosage forms include aqueous and nonaqueous solutions, emulsions, suspensions, and solutions and/or suspensions reconstituted from non-effervescent granules, containing suitable solvents, preservatives, emulsifying agents, suspending agents, diluents, sweeteners, coloring agents, and flavoring agents. When the compounds of the present invention are to be injected parenterally, they may be, e.g., in the form of an isotonic sterile solution. Alternatively, when the compounds of the present invention are to be inhaled, they may be formulated into a dry aerosol or may be formulated into an aqueous or partially aqueous solution.

In addition, when the compounds of the present invention are incorporated into oral dosage forms, it is contemplated that such dosage forms may provide an immediate release of the compound in the gastrointestinal tract, or alternatively may provide a controlled and/or sustained release through the gastrointestinal tract. A wide variety of controlled and/or sustained release formulations are well known to those skilled in the art, and are contemplated for use in connection with the formulations of the present invention. The controlled and/or sustained release may be provided by, e.g., a coating on the oral dosage form or by incorporating the compound(s) of the invention into a controlled and/or sustained release matrix.

Specific examples of pharmaceutically acceptable carriers and excipients that may be used to formulate oral dosage forms, are described in the *Handbook of Pharmaceutical Excipients*, American Pharmaceutical Association (1986), incorporated by reference herein. Techniques and compositions for making solid oral dosage forms are described in *Pharmaceutical Dosage Forms: Tablets* (Lieberman, Lachman and Schwartz, editors) 2nd edition, published by Marcel Dekker, Inc., incorporated by reference herein. Techniques and compositions for making tablets (compressed and molded), capsules (hard and soft gelatin) and pills are also described in *Remington's Pharmaceutical Sciences* (Arthur Osol, editor), 1553–1593 (1980), incorporated herein by reference. Techniques and composition for making liquid oral dosage forms are described in *Pharmaceutical Dosage Forms: Disperse Systems*, (Lieberman, Rieger and Banker, editors) published by Marcel Dekker, Inc., incorporated herein by reference.

When the compounds of the present invention are incorporated for parenteral administration by injection (e.g., continuous infusion or bolus injection), the formulation for parenteral administration may be in the form of suspensions, solutions, emulsions in oily or aqueous vehicles, and such formulations may further comprise pharmaceutically necessary additives such as stabilizing agents, suspending agents, dispersing agents, and the like. The compounds of the invention may also be in the form of a powder for reconstitution as an injectable formulation.

The dose of the compounds of the present invention is dependent upon the affliction to be treated, the severity of the symptoms, the route of administration, the frequency of the dosage interval, the presence of any deleterious side-effects, and the particular compound utilized, among other things.

A compound falling into the genus of PDE IV inhibitors of general formula (I) of the present invention is 3-(3-cyclopentyloxy-4-methoxybenzyl)-6-ethylamino-8-isopropyl-3H-purine. The compound 3-(3-cyclopentyloxy-4-methoxybenzyl)-6-ethylamino-8-isopropyl-3H-purine is disclosed and claimed in priority application Ser. No. 08/578,580, entitled "Novel Chemical Compounds Having PDE IV Inhibition Activity", which is hereby incorporated by reference.

Other compounds of the invention falling into the genus of PDE IV inhibitors of general formula (I), include:

6-amino-3 -(3-cyclopentyloxy-4-methoxy-benzyl)-8-isopropyl-3H-purine;

3 -(3 -cyclopentyloxy-4-methoxy-benzyl)-6-ethylamino-8-(1-hydroxy-1-methyl-ethyl)-3H-purine;

6-amino-3-(3-cyclopentyloxy-4-methoxy-benzyl)-8-(1-hydroxy-1-methyl-ethyl)-3H-purine;

6-ethylamino-3(3-((1RS, 3RS)-3-hydroxycyclopentyloxy)-4-methoxy-benzyl)-8-(1-hydroxy-1-methyl-ethyl)-3H-purine;

6-amino-3-(3-((1RS, 3RS)-3-hydroxycyclopentyloxy)-4-methoxy-benzyl)-8-(1-hydroxy-1-methyl-ethyl)-3H-purine;

6-ethylamino-3-(3-((1RS, 3RS)-3-hydroxycyclopentyloxy)-4-methoxy-benzyl)-8-isopropyl-3H-purine;

6-amino-3-(3 -((1RS, 3RS)-3 -hydroxycyclopentyloxy)-4-methoxy-benzyl)-8-isopropyl-3H-purine;

and pharmaceutically acceptable salts thereof

When certain of the above-identified compounds may exist in geometric or stereoisometric forms, the present invention contemplates all such compounds.

DETAILED DESCRIPTION OF PREFERRED EMBODIMENTS

The following examples illustrate various aspects of the invention.

EXAMPLE 1

6-Amino-3-(3-cyclopentyloxy-4-methoxy-benzyl)-8-isopropyl-3H-purine 3-(3-Cyclopentyloxy-4-methoxy-benzyl)-8-isopropyl-hypoxanthine (5.74 g, 15 mmole) and phosphorus oxychloride (60 ml) were heated to 65° C. for 30 minutes. The reaction mixture was evaporated to dryness in vacuo and the residue evaporated twice with toluene. The crude chloropurine (15 mmole) was dissolved in THF (80ml ) and 32% aqueous ammonia solution (36.2 ml) and heated together with liquid ammonia (50 g) in a 450 ml pressure reactor to 60° C. (340 psi) for 4 hours. The solvents were evaporated in vacuo and the residue suspended in a mixture of diethyl ether and 1 M NaOH solution. The solid was collected and crystallized from ethyl acetate to give the title compound, 3.92 g (68.5 %) mp 190–193° C.

Elemental analysis for $C_{21}H_{27}N_5O_2/381.48$. % calc: C, 66.12; H, 7.13; N, 18.36; O, 8.39. % found: C, 65.96; H, 6.95; N, 18.31; O, 8.61.

EXAMPLE 2

3-(3-Cyclopentyloxy-4-methoxy-benzyl)-6-ethylamino-8-(1-hydroxy-1-methyl-ethyl)-3H-purine hydrochloride A solution of 8-(1-benzyloxy-1-methyl-ethyl)-3-(3-cyclopentyloxy-4-methoxy-benzyl)- 6-ethylamino-3H-purine hydrochloride (1.65 g, 3 mmole) in methanol (25 ml) was hydrogenated with 10% Pd-C (0.17 g) and again after the addition of 25 ml of THF further 10% Pd-C (0.17 g) was added, and the mixture hydrogenated for 12 hours at room temperature. The catalyst was filtered off, the solvents were removed in vacuo, the residue was suspended in hot acetone and the solid collected at 0–5° C. to give the crude hydroxy-purine (1.10 g). This was dissolved in chloroform and filtered through 4.4 g of silicagel in a column. The purified product (0.84 g) was suspended in diethyl ether and the solid collected at 0–5° C. to give the title compound, 0.78 g (56.1%) mp 209–212° C.

Elemental analysis for $C_{23}H_{32}ClN_5O_3$/461.99. % calc: C, 59.80; H, 6.98; N, 15.16; O, 10.39. % found: C, 59.89; H, 7.10; N, 15.16; O, 10.60.

EXAMPLE 3

6-Amino-3-(3-cyclopentyloxy-4-methoxy-benzyl)-8-(1-hydroxy-1-methyl-ethyl)-3H-purine hydrochloride A solution of 6-amino-8-(1-benzyloxy-1-methyl-ethyl)-3-(3-cyclopentyloxy-4-methoxy-benzyl)-3H-purine hydrochloride (2.13 g, 4.06 mmole), in THF:methanol,1:1 (60 ml), was hydrogenated at room temperature and pressure with 10% Pd-C (0.26 g) for 12 hours. The catalyst was filtered off and the solvents removed in vacuo. The residue was suspended in hot acetone, the solid collected at 0–5° C. (1.23 g) and recrystallized from methanol-acetone to give the title compound, 0.76 g (43.2%) mp 231–232° C.

Elemental analyses for $C_{21}H_{28}ClN_5O_3 \cdot 0.5H_2O$. % calc: C, 56.69; H, 7.02; N, 15.74; O, 12.58. % found: C, 56.87; H, 6.86; N, 15.56; O, 12.75.

EXAMPLE 4

6-Ethylamino-3-(3-(3-hydroxycyclopentyloxy)-4-methoxy-benzyl)-8-(1-hydroxy-1-methyl-ethyl)-3H-purine hydrochloride A. 1-(3-Benzyloxy-4-methoxy-benzyl)-2-thiourea A solution of 3-hydroxy-4-methoxy-benzyl alcohol (61.67 g, 400 mmole) in 1-propanol (600 ml) was treated at 60° C. with 97% t-BuOK (55.52 g, 480 mmole), at 90° C. with benzyl chloride (66.57 ml, 560 mmole) and the resulting mixture heated under reflux for 2 hours. Then at 90° C. a second batch of t-BuOK (9.25 g, 80 mmole) was added. After a further hour at reflux a third batch of t-BuOK (9.25 g, 80 mmol) and a second batch of benzyl chloride (9.51 ml, 80 mmole) was added at 90° C. After a further 2.5 hours at reflux the mixture was cooled to room temperature and the solid filtered off. The solvents were removed in vacuo, the residue treated with water (300 ml) and one-third of the solvent removed in vacuo. Water (100 ml) was added to the residue, which was then distilled off in vacuo and the procedure repeated. The resulting suspension was filtered, the solid was collected, dried and triturated with petroleum ether (2×600 ml) to give 3-benzyloxy-4-methoxy-benzyl alcohol, (86.21 g, 88.2%) mp 62–65° C.

Thionyl chloride (64 ml) was added over 10 minutes to a stirred solution of the above alcohol in dichloromethane (500 ml). After 20 minutes the mixture was evaporated to dryness, in vacuo, toluene (2×75 ml) added, and evaporation in vacuo repeated to give crude 3-benzyloxy-4-methoxy-benzyl chloride (97.85 g, 105.5%). The chloride (353 mmole) was dissolved in acetone, (400 ml) treated with sodium thiocyanate, (57.22 g, 706 mmole) homogenized and heated under reflux for 1.5 hours. The solid was filtered off at room temperature and the solvent evaporated in vacuo. The residue was suspended in water (600 ml) to give a solution of pH 2, and neutralized with sodium bicarbonate solution. After crystallization the solid was collected, dried, dissolved in dichloromethane (300 ml), dried ($Na_2SO_4$), treated with charcoal, filtered and evaporated to dryness. The residue was crystallized from petroleum ether (400 ml) to give 3-benzyloxy-4-methoxy-benzyl thiocyanate (95.65 g, 95.0%), mp 70–74° C. The thiocyanate (335 mmole) was heated under reflux in n-valeronitrile (280ml) for 2 hours and evaporated to dryness to give 98.4 g of crude product. This was dissolved in THF (200 ml) and treated with 32% aqueous ammonia solution (101 ml) at room temperature. After 3 hours the thiourea was collected at 10° C. and washed with diethyl ether to give 1-(3-benzyloxy-4-methoxy-benzyl)-2-thiourea (63.08 g, 62.2%), mp 179–181° C. The filtrate was evaporated to dryness and the residue crystallized from dichloromethane to give 11.51 g (11.3%) as a second crop.

B. 6-Amino-1-(3-benzyloxy-4-methoxy-benzyl)-2-thiouracil 1-(3-Benzyloxy-4-methoxy-benzyl)-2-thiourea (72.58 g, 240 mmole) was added to a solution of 97% t-BuOK (30.54 g, 264 mmole) in isopropanol (300 ml), the mixture heated under reflux until dissolution was complete, then ethyl cyanoacetate (26.1 ml, 245 mmole) was added. After 5 hours at reflux, the mixture was cooled slightly, another batch of t-BuOK (2.78 g, 24 mmole) and ethyl cyanoacetate (5.12 ml, 48 mmole) was added, and the mixture heated under reflux for a further 15 hours. The reaction mixture was cooled to room temperature, poured onto water (1.21) and neutralized with cooling to pH 8 with 5M HCl (43 ml). After 1 hour stirring the solid was collected at 10° C. and washed first with water (180 ml), then saturated sodium bicarbonate solution (60 ml), isopropanol (60 ml) and finally cold water (500 ml). The crude material was suspended in 0.5M NaOH (1.4 l) and isopropanol (350 ml). The insoluble part was filtered off and washed with 0.1M NaOH and water to give recovered thiourea (10.45 g, 14.4%). The filtrate was neutralized to pH 8 with 2M phosphoric acid (175 ml), crystallized over night, the solid collected and washed with the above three component liqours and water to give the crude thiouracil (73.33 g). This product was suspended in hot acetone (600 ml), concentrated to 500 ml and collected at 0–5° C. to give 6-amino-1-(3-benzyloxy-4-methoxy-benzyl)-2-thiouracil (65.73 g, 74.1%), mp 239–240° C.

C. 1-(3-Benzyloxy-4-methoxy-benzyl)-5,6-di amino-2-thiouracil 6-amino-1-(3-benzyloxy-4-methoxy-benzyl)-2-thiouracil (36.94 g, 100 mmole) was dissolved in DMSO (74 ml), diluted with THF (185 ml) and treated with 85% phosphoric acid (7.46 ml). At 55–60° C., 4M sodium nitrite (30 ml, 120 mmole) was added slowly. After 30 minutes, methanol (10 ml) was added, the reaction was cooled to 30° C., and a suspension of 85% sodium dithionite (40.96 g, 200 mmole) in water (80 ml) was added slowly. After the addition of water (200 ml) the solvent was removed in vacuo and the suspension diluted with water to 1 l. The solid was collected at 0–5° C. to give crude 1-(3-benzyloxy-4-methoxy-benzyl)-5,6-diamino-2-thiouracil (40.58 g).

D. 6-Amino-1-(3-benzyloxy-4-methoxy-benzyl)-5-(2-benzyloxy-2-methyl-propionylamino)-2-thiouracil A solution of 2-benzyloxy-2-methyl-propionyl chloride (30.70 g, 144 mmole) in THF (100 ml) was added at 0–5°

C. over 15 minutes to a stirred suspension of 1-(3-benzyloxy-4-methoxy-benzyl)-5,6-diamino-2-thiouracil (40.58 g, 100 mmole) and triethylamine (31.4 ml, 225 mmole) in THF (400 ml). After 1 hour the solid was filtered off and the solution evaporated to dryness in vacuo. The residue was suspended in a mixture of diethyl ether (400 ml), water (100 ml) and saturated sodium bicarbonate solution (60 ml). After crystallization for 60 hours the solid was collected and washed with ether and water to give 6-amino-1-(3-benzyloxy-4-methoxy-benzyl)-5-(2-benzyloxy-2-methyl-propionylamino)-2-thiouracil (42.23 g, 75.3%). Crystallization from ethyl acetate gave mp 123–125/ 184–187° C.

E. 3-(3-Benzyloxy-4-methoxy-benzyl)-8-(1-benzyloxy-1-methyl-ethyl)-2-thioxanthine 6-Amino-1-(3-benzyloxy-4-methoxy-benzyl)-5-(2-benzyloxy-2-methyl-propionylamino)-2-thiouracil (46.54 g, 83 mmole) and 97% t-BuOK (38.41 g, 332 mmole) were heated under reflux in isopropanol (460 ml) for 50 minutes. The solvent was removed in vacuo, the residue dissolved in water (300 ml), treated twice with 5 g of charcoal, filtered, water added to a total volume of 500 ml and pH adjusted to neutral with a mixture of 5M HCl (60 ml) and sodium bicarbonate solution. The solid was collected at 10° C. to give 41.62 g of crude product, which was dissolved in dichloromethane (60 ml) and chromatographed over silica-gel (126 g) using dichloromethane as eluant. Crystallization from methanol gave 3-(3-benzyloxy-4-methoxy-benzyl)-8-(1-benzyloxy-1-methyl-ethyl)-2-thioxanthine, (31.5 g, 69.9%) mp 290–302° C. (dec).

F. 3-(3-Benzyloxy-4-methoxy-benzyl)-8-(1-benzyloxy-1-methyl-ethyl)-hypoxanthine 3-(3-Benzyloxy-4-methoxy-benzyl)-8-(1-benzyloxy-1-methyl-ethyl)-2-thioxanthine (26.05 g, 48 mmole) was heated under reflux in 1-propanol (700 ml) with Raney-nickel (29 g) (treated with 0.1% aqueous acetic acid) for 1.5 hours. The nickel was filtered off and the solvent evaporated in vacuo. The residue was dissolved in dichloromethane (300 ml), extracted with sodium carbonate solution and evaporated again to dryness. The residue was dissolved in methanol (150 ml), treated with charcoal, filtered, concentrated and crystallized to give 3-(3-benzyloxy-4-methoxy-benzyl)-8-(1-benzyloxy-1-methyl-ethyl)-hypoxanthine (15.81 g, 64.5%), mp 78–86° C. (containing methanol). A second crop gave 2.29 g (9.3%) of hypoxanthine.

G. 3-(3-Benzyloxy-4-methoxy-benzyl)-8-(1-benzyloxy-1-methyl-ethyl)-6-ethylamino-3H-purine hydrochloride 3-(3-Benzyloxy-4-methoxy-benzyl)-8-(1-benzyloxy-1-methyl-ethyl)-hypoxanthine (3.06 g, 6 mmole) was treated twice with toluene and evaporated to dryness to remove residual methanol from the previous step, and then heated to 70° C. with phosphorus oxychloride (30 ml). After 40 minutes the reaction mixture was evaporated in vacuo to dryness and after the addition of toluene repeated twice. The crude chloropurine was dissolved in THF (50 ml) and added slowly to 70% aqeous ethylamine (24 ml) with cooling. After 30 minutes the reaction mixture was evaporated to dryness in vacuo. The residue was dissolved in dichloromethane (50 ml), extracted with 1M NaOH solution and evaporated again. The residue was dissolved in methanol (25 ml), treated with 1M methanolic HCI (6.1 ml) and evaporated to dryness in vacuo to give crude 3-(3-benzyloxy-4-methoxy-benzyl)-8-(1-benzyloxy-1-methyl-ethyl)-6-ethylamino-3H-purine hydrochloride (3.31 g, 96.2%).

H. 6-Ethylamino-3-(3-hydroxy-4-methoxy-benzyl)-8-(1-hydroxy-1-methyl-ethyl)-3H-purine hydrochloride The above crude 3-(3-benzyloxy-4-methoxy-benzyl)-8-(1-benzyloxy-1-methyl-ethyl)-6-ethylamino-3H-purine hydrochloride (3.28 g, 5.7 mmole) was hydrogenated at room temperature and pressure in a mixture of THF:methanol 1:1 (60 ml) with 10% Pd-C (0.66 g). The catalyst was filtered off, the solvents evaporated in vacuo and the residue crystallized from acetone to give 6-ethylamino-3-(3-hydroxy-4-methoxy-benzyl)-8-(1-hydroxy-1-methyl-ethyl)-3H-purine hydrochloride (1.80 g, 80.0%), mp 184–185° C.

I. 6-Ethylamino-3-(3-(3-hydroxycyclopentyloxy)-4-methoxy-benizyl)-8-(1-hydroxy-1-methyl-ethyl)-3H-purine hydrochloride A solution of 6-ethylamino-3-(3-hydroxy-4-methoxy-benzyl)-8-(1-hydroxy-1-methyl-ethyl)-3H-purine hydrochloride (1.18 g, 3 mmole) in DMF (12 ml) and potassium carbonate (2.49 g, 18 mmole) was treated at room temperature with crude cis-trans 3-bromocyclopentanol (1.49 g, 9 mmole) (prepared from cis-trans 1,3-cyclopentanediol and triphenylphosphine dibromide). After 72 hours a second portion of potassium carbonate (0.62 g, 4.5 mmole) and cis-trans 3-bromocyclopentanol (0.74 g, 4.5 mmole) was added. After 6 days the solid was filtered off and the solution evaporated in vacuo and repeated four times with water. The residue was dissolved in dichloromethane, extracted with 1M NaOH and evaporated to dryness. The residue (1.71 g) was dissolved in methanol (20 ml), treated with 1M methanolic HCl (3.2 ml) and evaporated to dryness in vacuo. The residue was crystallized from acetone and recrystallized from methanol-acetone to give crude product (1.02 g). The impure crystals were dissolved in THF (70 ml) and extracted four times with 2M NaOH and once with sodium chloride solution, evaporated to dryness, taken up in dichloromethane, dried with soduim sulfate, filtered and evaporated to dryness. The free base was again converted to the HCl salt and crystallized from acetone to give 0.78 g (54.6%) of title compound, mp 180–185° C.

Elemental analyses for $C_{23}H_{32}ClN_5O_4$ with 1% HCl and 1% $H_2O$. % calc: C, 56.63; H, 6.76; N, 14.36 O, 14.01; Cl, 8.24. % found: C, 56.30; H, 6.80; N, 14.48 O, 13.99 Cl, 7.92.

EXAMPLE 5

6-Amino-3-(3-(3-hydroxycyclopentyloxy)-4-methoxy-benzyl)-8-(1-hydroxy-1-methyl-ethyl)-3H-purine hydrochloride A. 6-Amino-3-(3-benzyloxy-4-methoxy-benzyl)-8-(1-benzyloxy-1-methyl-ethyl)-3H-purine hydrochloride 3-(3-Benzyloxy-4-methoxy-benzyl)-8-(1-benzyloxy-1-methyl-ethyl)-hypoxanthine (Example 4F) (3.06 g, 6 mmole) was treated twice with toluene and evaporated to dryness to remove residual methanol from the previous step, then heated to 70° C. with phosphorus oxychloride (30 ml). After 35 min the solution was evaporated to dryness in vacuo and after the addition of toluene repeated twice. The crude chloro compound was dissolved in THF (40ml) and added to 32% aqueous ammonia (12 ml) with cooling in a 450 ml pressure reactor. After the addition of liquid ammonia (50 ml) at −30° C. the reaction mixture was heated to 60° C. (340 psi) for 3 hours. The solid was filtered off and the solvents evaporated in vacuo. The residue was dissolved in dichloromethane (40 ml), extracted with 1M NaOH (2×10 ml) and evaporated again to dryness. The residue was dissolved in methanol, treated with 1M methanolic HCl solution (6.2 ml) and evaporated to dryness in vacuo to give slightly impure 6-amino-3-(3-benzyloxy-4-methoxy-benzyl)-8-(1-benzyloxy-1-methyl-ethyl)-3H-purine hydrochloride, (3.22 g, 98.2%) mp 189–190° C. (after crystallisation from acetone).

B. 6-Amino-3-(3-hydroxy-4-methoxy-benzyl)-8-(1-hydroxy-1-methyl-ethyl)-3H-purine hydrochloride A solution of the above 6-amino-3-(3-benzyloxy-4-methoxy-benzyl)-8-(1-benzyloxy-1-methyl-ethyl)-3H- purine hydrochloride (3.22 g) in THF:methanol (1:1) (60 ml) was hydrogenated at room temperature and pressure for 2.5 hours with 10% Pd-C (0.64 g). The catalyst was filtered off and the solution evaporated to dryness in vacuo. The residue was crystallized from acetone to give 6-amino-3-(3-hydroxy-4-methoxy-benzyl)-8-(1-hydroxy-1-methyl-ethyl)-3H-purine hydrochloride, (1.67 g, 77.3%) mp 155–160° C.

C. 6-Amino-3-(3-(3-hydroxycyclopentyloxy)-4-methoxy-benzyl)-8-(1-hydroxy-1-methyl-ethyl)-3H-purine hydrochloride A stirred solution of 6-amino-3-(3-hydroxy-4-methoxy-benzyl)-8-(1-hydroxy-1-methyl-ethyl)-3H-purine hydrochloride (1.46 g, 4 mmole) in DMF (15 ml) was treated with potassium carbonate (3.46 g, 25 mmole) and cis-trans 3-bromocyclopentanol (2.53 g, 15.31 mmole). After 3 days at room temperature a second batch of potassium carbonate of (1.1 g, 8 mmole) and 3-bromocyclopentanol (1.33 g, 8.1 mmole) was added. After 10 days the solid was filtered off and the solution evaporated in vacuo. The solid was dissolved in dichloromethane (70 ml), extracted twice with 1M NaOH (20 ml) and evaporated to dryness in vacuo. The residue was dissolved in methanol (20 ml), treated with 1M methanolic HCl solution (4 ml) and evaporated again to dryness in vacuo. The residue was crystallized from acetone to give dihydroxyadenine (1.08 g, 60.0%), which was dissolved in water (30 ml), treated with a small amount of ether and 10M NaOH solution (3 ml). After 72 hours the crystals were collected, dried and recrystallized from water saturated ethyl acetate to give the title compound, (0.66 g, 40.0%) mp 98–108° C., trans-cis ratio about 4:1.by 250 MHz N.M.R.

Elemental analyses for $C_{21}H_{27}N_5O_4$ with 10.2% of water. % calc: C, 54.78; H, 7.05; N, 15.21; O, 22.96. % found: C, 54.47; H, 7.05; N, 15.12; O, 22.64.

EXAMPLE 6

6-Ethylamino-3-(3-(3-hydroxycyclopentyloxy)-4-methoxy-benzyl)-8-isopropyl-3H-purine hydrochloride A. 6-Amino- -(3-benzyloxy-4-methoxy-benzyl)-5-isobutyrylamino-2-thiouracil 4M sodium nitrite solution (46.6 ml, 186 mmole) was added within 5 minutes at 55° C. with stirring to a solution of 6-amino-1-(3-benzyloxy-4-methoxy-benzyl)-2-thiouracil (53.00 g, 144 mmole) and 85% phosphoric acid (12.09 ml, 179 mmole) in DMF (550 ml). After 1.5 hours the reaction mixture was cooled to 35° C. and treated with a suspension of 85% sodium dithionite (58.77 g, 287 mmole) in water (138 ml). After 30 minutes isobutyric anhydride (72 ml, 215 mmole) was added. After 1 hour the suspension was diluted slowly with 1M NaOH (790 ml) and water (1950 ml) (pH changed from 3 to 7). After stirring over night sodium bicarbonate (24.2 g) was added to give a pH of 7.5. The solid was collected, washed with 0.2M sodium bicarbonate solution followed by water, then dried to give crude thiouracil (56.10 g, 86.0%). Trituration with acetone gave 6-amino-1-(3-benzyloxy-4-methoxy-benzyl)-5-isobutyrylamino-2-thiouracil, mp 240–244° C.

B. 3-(3-Benzyloxy-4-methoxy-benzyl)-8-isopropyl-2-thioxanthine

6-Amino-1-(3-benzyloxy-4-methoxy-benzyl)-5-isobutyrylamino-2-thiouracil (56.10 g, 123 mmole) was heated under reflux in 1M NaOH (560 ml) solution for 40 minutes. After cooling to room temperature the solid was removed by filtration, the solution treated twice with charcoal (2.7 g), filtered and neutralized with 5M HCl (95 ml) to pH 8. The solid was collected, washed with 0.1 M sodium bicarbonate solution and water then dried to give crude product (38.65 g, 71.7%). Crystallization from THF and methanol gave still impure product (34.65 g), which was dissolved in 1M NaOH (340 ml), treated twice with charcoal (3.4 g), filtered, diluted with methanol (80 ml) and neutralized with 85% phosphoric acid (13 ml). The solid was collected and washed with water (1.5l) until a neutral pH to give 3-(3-benzyloxy-4-methoxy-benzyl)-8-isopropyl-2-thioxanthine (28.99 g, 53.8%), mp 280–281° C.

C. 3-(3-benzyloxy-4-methoxy-benzyl)-8-isopropyl-hypoxanthine 3-(3-Benzyloxy-4-methoxy-benzyl)-8-isopropyl-2-thioxanthine (21.83 g, 50 mmole) was heated under reflux in 1-propanol (700 ml) with Raney-nickel (30 g) (pre-treated with 0.1% of aqueous acetic acid). After 4 hours the nickel was filtered off and washed with hot propanol and chloroform. The solution was evaporated to dryness in vacuo. The residue was dissolved in chloroform, extracted with IM sodium carbonate solution, dried ($Na_2SO_4$), treated twice with charcoal (0.8 g), filtered and evaporated to dryness in vacuo. The residue was suspended in hot acetone (250 ml), concentrated and the solid collected at 0–5° C. to give 3-(3-benzyloxy-4-methoxy-benzyl)-8-isopropyl-hypoxanthine (15.27 g, 75.5%), mp 233–235° C.

D. 3-(3-Benzyloxy-4-methoxy-benzyl)-6-ethylamino-8-isopropyl-3H-purine hydrochloride 3-(3-Benzyloxy-4-methoxy-benzyl)-8-isopropyl-hypoxanthine (2.02 g, 5 mmole) and phosphorus oxychloride (20 ml) were heated to 70° C. for 35 min. The solution was evaporated to dryness and evaporation repeated twice after the addition of toluene (50 ml). The crude chloropurine residue was dissolved in THF (20 ml) and added at 0–5° C. to 70% aqueous ethylamine (20 ml). After 1 hour at room temperature the solvents were removed in vacuo, the residue was dissolved in dichloromethane (70 ml) and washed with 1M NaOH. The organic phase was filtered through 9 g of silicagel in a column and evaporated to dryness in vacuo. The residue was dissolved in methanol (20 ml), treated with 1M methanolic HCl (4.8 ml) and evaporated to dryness in vacuo to give 3-(3-benzyloxy-4-methoxy-benzyl)-6-ethylamino-8-isopropyl-3H-purine hydrochloride (2.20 g, 94.0%), mp 79–83° C. (after crystallization from water-saturated ether).

E. 6-Ethylamino-3-(3-hydroxy -4-methoxy-benzyl)-8-isopopyl-3H-purine hydrochloride A solution of the above 3-(3-hydroxy-4-methoxy-benzyl)-6-ethylamino-8-isopropyl-3H-purine hydrochloride (2.20 g; 4.7 mM) in THF-methanol (1:1) (140 ml) was hydrogenated for 1 hour with 10% Pd-C (0.44 g). The catalyst was filtered off and the solution evaporated to dryness in vacuo. The residue was crystallized from ethyl acetate to give the title compound (1.64 g,92.1%), mp 156–160° C.

F. 6-Ethylamino-3-(3-(3-hydroxycyclopentyloxy)-4-methoxy-benzyl )-8-isopropyl-3H-purine hydrochloride A solution of 3-(3-hydroxy -4-methoxy-benzyl)-6-ethylamino-8-isopopyl-3H-purine hydrochloride (0.76 g, 2 mmole) in DMF (8 ml) at room temperature was treated with potassium carbonate (1.66 g, 12 mmole) and after 1 hour with crude cis-trans 3-bromocyclopentanol (0.99 g, 6 mmole). After stirring for 18 hours another batch of potassium carbonate (0.83 g, 6 mmole) and 3-bromocyclopentanol (0.99 g, 6 mmole) were added. After a further 24 hours the solid was filtered off and the solution evaporated to dryness in vacuo. After the addition of water the evaporation was repeated four times. The residue was dissolved in chloroform (50ml) and extracted with IM NaOH solution (2×20 ml). The organic phase was evaporated to dryness in vacuo. The residue (1.35 g) was dissolved in dichloromethane:methanol, 98:2 (5 ml) and purified by column chromatography on 30 g of silicagel. The crude product (0.16 g) was dissolved in methanol (5 ml), treated with 1M methanolic HCl (0.4 ml) and evaporated to dryness in vacuo. The residue was crystallized from ethyl acetate to give the title compound, (0.15 g, 16.2%) mp 165–169° C.

Elemental analyses for $C_{23}H_{32}ClN_5O_3$. % calc: C, 59.80; H, 6.98; N, 15.16; O, 10.39. % found: C, 59.60; H, 6.99; N, 15.02; O, 10.58.

EXAMPLE 7

6-Amino-3-(3-(3-hydroxycyclopentyloxy)-4-methoxy-benzyl)-8-isopropyl-3H-purine hydrochloride A. 6-Amino-3-(3-benzyloxy-4-methoxy-benzyl)-8-isopropyl-3 H-purine hydrochloride 3-(3-Benzyloxy-4-methoxy-benzyl)-8-isopropyl-hypoxanthine (Example 6C) (4.04 g, 10 mmole) and phosphorus oxychloride (40 ml) were heated to 70° C. for 35 minutes. The reaction mixture was evaporated to dryness in vacuo and, after the addition of toluene, evaporation repeated twice. The crude chloropurine was dissolved in THF (40 ml) and added slowly with cooling to 32% aqueous ammonia (12 ml, 200 mmole) in a 450 ml pressure reactor. After the addition of liquid ammonia (50 g) at −30° C. the mixture was heated to 60° C. (340 psi) for 3 hours. The solid was filtered off and the solution evaporated to dryness in vacuo. The residue was suspended in water (100 ml) and the mixture filtered to give the crude product (4.09 g) as a crystalline solid. This was dissolved in methanol (60 ml), treated with 1M methanolic HCl solution (10 ml), evaporated to dryness in vacuo, suspended in acetone and filtered to give 6-amino-3-(3-benzyloxy-4-methoxy-benzyl)-8-isopropyl-3H-purine hydrochloride (4.04 g, 91.8%), as a crystalline solid mp 200° C., (sublimation)/240–243° C.

B. 6-Amino-3-(3-hydroxy-4-methoxy-benzyl)-8-isopropyl-3H-purine hydrochloride hydrate 6-Amino-3-(3-benzyloxy-4-methoxy-benzyl)-8-isopropyl-3H-purine hydrochloride (4.04 g, 9.2 mmole), in THF:methanol (1:1) (600 ml) was hydrogenated for 10 hours over 10% Pd-C (0.8 g) at room temperature and pressure. The catalyst was filtered off, the solvents removed in vacuo and the residue crystallized from acetone to give 6-amino-3-(3-hydroxy-4-methoxy-benzyl)-8-isopropyl-3H-purine hydrochloride (2.53 g, 78.8%), mp 125-130/185–195° C.

Elemental analyses for $C_{16}H_{20}ClN_5O_2$ with 1 $H_2O$/ 367.84. % calc: C, 52.25; H, 6.03; N, 19.04; O, 13.05. % found: C, 52.55; H, 5.96; N, 19.05; O, 12.55

C. 6-Amino-3-(3-(3-hydroxycyclopentyloxy)-4-methoxy-benzyl)-8-isopropyl-3H-purine hydrochloride A solution of 6-amino-3-(3-hydroxy-4-methoxy-benzyl)-8-isopropyl-3H-purine hydrochloride (2.45 g, 7.0 mmole) in DMF (25 ml) was treated with potassium carbonate (5.80 g, 42 mmol), the mixture stirred at room temperature for 1 hour, then crude cis/trans-3-bromocyclopentanol (3.47 g, 21 mmole) was added. After 21 hours a second batch of potassium carbonate (2.90 g, 21 mmole) and 3-bromocyclopentanol (3.47 g, 21 mmole) were added. After stirring for 6 days the solid was filtered off and the solvent evaporated to dryness in vacuo. The residue was dissolved in chloroform (50 ml), extracted with IM NaOH solution and again evaporated in vacuo. The residue (5.84 g) was dissolved in dichloromethane:methanol, 98:2 (50 ml) and purified by column chromatography on silicagel, eluting with a gradient of 2–10% of methanol in dichloromethane. The fractions were collected (0.78 g; 28.0%), converted to the HCl salt and crystallized from acetone to give the title compound, (0.55 g, 18.1%), mp 185–187° C.

Elemental analyses for $C_{21}H_{28}ClN_5O_3$/433.94. % calc: C, 58.13; H, 6.50; N, 16.14; O, 11.06. % found: C, 57.84; H, 6.60; N, 16.10) 11.39.

Enzyme Isolation Protocols

Protocols for obtaining PDE III, PDE IV and PDE V, and measuring inhibition activities are set forth below:

Type III Phosphodiesterase

Protocol for Enzyme Isloation: The Type III PDE is isolated from human platelets using a procedure similar to that previously described by Weishaar, R. E.; Burrows, S. D.; Kobylarg, D. C., Quade, N. M.; Evans, D. B., Biochem. Pharmacol., 35:787, 1986. Briefly, 1–2 units of platelets arc suspended in an equal volume of buffer (20 mM Tris-HCl, pH 7.5, containing 2 mM magnesium acetate, 1 mM dithiothreitol, and 5 mM $Na_2EDTA$). The protease inhibitor phenylmethyl-sulfonyl fluoride (PMSF) is also included in this buffer at a final concentration of 200 mM. The suspension is homogenized using a polytron and the homogenate centrifuged at 100,000×g for 60 minutes. This and all subsequent procedures are performed at 0–4° C. The supernatant is then filtered through four layers of gauze and applied to a DEAE-Trisacryl M column, previously equilibrated with buffer B (20 mM Tris-HCl, pH 7.5, containing 1 mM magnesium acetate, 1 mM dithiothreitol and 200 mM PMSF). After application of the sample, the column is washed with several bed volumes of buffer B, after which the different forms of PDE are eluted from the column using two successive linear NaCl gradients (0.05–0.15 M, 300 ml total; 0.15–0.40 M, 200 ml total). Five milliliter fractions are collected and assayed for cyclic AMP and cyclic GMP PDE activity. Fractions containing PDE III activity are pooled and dialyzed overnight against 4 liters of buffer B. The dialyzed PDE III is then concentrated to 10% of the original volume, diluted to 50% with ethylene glycol monoethyl ether and stored at −20° C. PDE III can typically be retained for up to four weeks with little or no loss of activity.

Measuring Type III PDE Activity: Enzyme activity is assessed by measuring the hydrolysis of [$^3H$]-cyclic AMP, as described by Thompson, W. J., Teraski, W. L., Epstein, P. N., Strada, S. J.: Adv. Cyclic Nucleotide Res. 10:69, 1979. The cyclic AMP concentration used in this assay is 0.2 mM, which approximates to the $K_m$ value. Protein concentration is adjusted to ensure that no more than 15% of the available substrate is hydrolyzed during the incubation period.

All test compounds are dissolved in dimethyl sulfoxide (final concentration of 2.5%). This concentration of dimethyl sulfoxide inhibits enzyme activity by approximately 10%.

Type IV Phosphodiesterase

Protocol for Enzyme Isolation: The Type IV PDE is isolated from bovine tracheal smooth muscle using a procedure similar to that previously described by Silver, P. J., et al.: Eur. J. Pharmacol. 150:85, 1988.(1). Briefly, smooth muscle from bovine trachea is minced and homogenized using a polytron in 10 volumes of an extraction buffer containing 10 mM Tris-acetate (pH 7.5), 2 mM magnesium chloride, 1 mM dithiothreitol and 2,000 units/ml of aprotinin. This and all subsequent procedures are performed at 0–4° C. The homogenate is sonicated and then centrifuged at 48,000×g for 30 minutes. The resulting supernatant is applied to a DEAE Trisacryl M column previously equilibrated with sodium acetate and dithiothreitol. After applications of the sample, the column is washed with sodium acetate/dithiothreitol, after which the different forms of PDE are eluted from the column using a linear Tris-HCl/NaCl gradient. Fractions containing Type IV PDE are collected, dialyzed and concentrated to 14% of the original volume. The concentrated fractions are diluted to 50% with ethylene glycol and stored at −20° C.

Measuring Type IV PDE Activity: Enzyme activity is assessed by measuring the hydrolysis of [$^3$H]-cyclic AMP, as described by Thompson, W. J., et al.: Adv. Cyclic Nucleotide Res. 10:69, 1979. The cyclic AMP concentration used in this assay is 0.2 mM, which approximates to the $K_m$ value. Protein concentration is adjusted to ensure that no more than 15% of the available substrate is hydrolyzed during the incubation period.

All test compounds are dissolved in dimethyl sulfoxide (final concentration of 2.5%). This concentration of dimethyl sulfoxide inhibits enzyme activity by approximately 10%.

Measuring Type V PDE Activity

Protocol for Enzyme Isolation: The Type V PDE is isolated using a procedure similar to that previously described by Weishaar et al., Hypertension 15:528, (1990). Briefly, 1–2 units of platelets are suspended in an equal volume of buffer A (20 mM Tris-HCl, pH 7.5, containing 2 mM magnesium acetate, 1 mM dithiothreitol, and 5 mM Na$_2$EDTA) using a polytron. The proteinase inhibitor phenylmethylsulfonyl fluoride (PMSF) are also included in this buffer at a final concentration of 200 uM. This and all subsequent procedures are performed at 0–4° C. The homogenate is then centrifuged at 100,000 rpm for 60 minutes. The supernatant is then removed and filtered through four layers of gauze and applied to a DEAE-Trisacryl M column. The column is washed with several bed volumes of buffer B (20 mM Tris-HCl, pH 7.5, containing 2 mM magnesium acetate, 1 mM dithiothreitol, and 200 mM PMSF) and eluted by two successive linear NaCl gradients (0.05–0.15 M, 300 ml total; 0.15– 0.40 M, 200 ml total). Five ml fractions are collected and assayed for cyclic AMP and cyclic GMP PDE activity. Fractions that contain PDE V are pooled and dialyzed overnight against 4 L of buffer C (20 mM Tris-HCl, pH 7.5, containing 2 mM magnesium acetate and proteinase inhibitors). The dialyzed PDE V is then concentrated to 10% of the original volume, diluted to 50% with ethylene glycol monoethyl ether and stored at −20° C. PDE V can typically be retained for up to four weeks with little or no loss of activity.

Measuring Type V PDE Activity: Enzyme activity is assessed by measuring the hydrolysis of [$^3$H]-cyclic GMP, as described by Thompson et al. (Thompson, W. J., Teraski, W. L., Epstein, P. N., Strada, S. J.: Adv. Cyclic Nucleotide Res. 10:69, 1979). The cyclic GMP concentration used in this assay is 0.2 uM, which approximates to the $K_m$ value. Protein concentration is adjusted to ensure that no more than 15% of the available substrate is hydrolyzed during the incubation period.

All test compounds are dissolved in dimethyl sulfoxide (final concentration of 2.5%). This concentration of dimethyl sulfoxide inhibits enzyme activity by approximately 10%. The reference Type V PDE inhibitor zaprinast is evaluated with each assay.

The compounds are tested over concentration range: 0.1, 1, 10, 100 uM (n=1), and IC$_{50}$ determinations are made using 5 appropriate concentrations (n=2).

As can be seen from the foregoing, the compositions of the present invention are also potent inhibitors of PDE V in mammals. Such activity is useful in the medical arts to reduce smooth muscle cell proliferation and increase pulmonary vasodilation. In certain aspects of the invention, the compounds demonstrate a combination of selective PDE IV and PDE V inhibition and can be used in diseases such as restenosis and related diseases. Such aspects, of course, include administering an effective amount of a compound of the present invention possessing said combination of PDE IV and V inhibitory activities to a mammal in need of such therapy.

Following the above procedures, the PDE III, PDE IV and PDE V inhibition for the compounds of Examples 1–5 were tested and compared. The results are shown in Table I below:

TABLE I

| EXAMPLE | PDE III IC$_{50}$($\mu$M) | PDE IV IC$_{50}$($\mu$M) | PDE V IC$_{50}$(micro M) |
| --- | --- | --- | --- |
| 1 | 381 | 0.82 | 373 |
| 2 | 257 | 0.19 | 30.5 |
| 3 | >1000 | 0.25 | 800 |
| 4 | >1000 | 0.59 | >1000 |
| 5 | >1000 | 2.25 | >1000 |

While the invention has been illustrated with respect to the production and use of particular compounds, it is apparent that variations and modifications of the invention can be made without departing from the spirit or scope of the invention.

What is claimed is:

1. A pharmaceutical composition comprising a pharmaceutically acceptable carrier and a compound selected from the group consisting of:

6-amino-3-(3-cyclopentyloxy-4-methoxy-benzyl)-8-isopropyl-3H-purine;

3-(3-cyclopentyloxy-4-methoxy-benzyl)-6-ethylamino-8-(1-hydroxy-1-methyl-ethyl)-3H-purine;

6-amino-3-(3-cyclopentyloxy-4-methoxy-benzyl)-8-(1-hydroxy-1-methyl-ethyl)-3H-purine;

6-ethylamino-3-(3-((1RS, 3RS)-3-hydroxycyclopentyloxy)-4-methoxy-benzyl)-8-(1-hydroxy-1-methyl-ethyl)-3H-purine;

6-amino-3-(3 -((1RS, 3RS)-3-hydroxycyclopentyloxy)-4-methoxy-benzyl)-8-(1-hydroxy-1-methyl-ethyl)-3H-purine;

6-ethylamino-3-(3-((1RS, 3RS)-3-hydroxycyclopentyloxy)-4-methoxy-benzyl)-8-isopropyl-3H-purine;

6-amino-3-(3 -((1RS, 3RS)-3-hydroxycyclopentyloxy)-4-methoxy-benzyl)-8-isopropyl-3H-purine;

pharmaceutically acceptable salts thereof; and stereoisometric forms thereof.

2. The pharmaceutical composition of claim 1 wherein said compound is selected from the group consisting of 6-amino-3-(3-cyclopentyloxy-4-methoxy-benzyl)-8-isopropyl-3H-purine, and pharmaceutically acceptable salts thereof.

3. The pharmaceutical composition of claim 2 which is suitable for oral administration.

4. The pharmaceutical composition of claim 2 which is suitable for administration by inhalation.

5. The pharmaceutical composition of claim 2 which is suitable for parenteral administration.

6. A compound selected from the group consisting of:
- 6-amino-3-(3-cyclopentyloxy-4-methoxy-benzyl)-8-isopropyl-3H-purine;
- 3-(3 -cyclopentyloxy-4-methoxy-benzyl)-6-ethylamino-8-(1-hydroxy-1-methyl-ethyl)-3H-purine;
- 6-amino-3-(3-cyclopentyloxy-4-methoxy-benzyl)-8-(1-hydroxy-1-methyl-ethyl)-3H-purine;
- 6-ethylamino-3(3-((1RS, 3RS)-3-hydroxycyclopentyloxy)-4-methoxy-benzyl)-8-(1-hydroxy-1-methyl-ethyl)-3H-purine;
- 6-amino-3-(3-((1RS, 3RS)-3-hydroxycyclopentyloxy)-4-methoxy-benzyl)-8-(1-hydroxy-1-methyl-ethyl)-3H-purine;
- 6-ethylamino-3-(3-((1RS, 3RS)-3-hydroxycyclopentyloxy)-4-methoxy-benzyl)-8-isopropyl-3H-purine;
- 6-amino-3-(3-((1RS, 3RS)-3-hydroxycyclopentyloxy)-4-methoxy-benzyl)-8-isopropyl-3H-purine;
- and pharmaceutically acceptable salts thereof, and stereoisometric forms thereof.

7. The pharmaceutical composition of claim 1 wherein said compound is selected from the group consisting of 3-(3-cyclopentyloxy-4-methoxy-benzyl)-6-ethylamino-8-(1-hydroxy-1-methyl-ethyl)-3H-purine, and pharmaceutically acceptable salts thereof.

8. The pharmaceutical composition of claim 3 which is suitable for oral administration.

9. The pharmaceutical composition of claim 7 which is suitable for administration by inhalation.

10. The pharmaceutical composition of claim 7 which is suitable for parenteral administration.

11. The pharmaceutical composition of claim 1 wherein said compound is selected from the group consisting of 6-amino-3-(3-cyclopentyloxy-4-methoxy-benzyl)-8-(1-hydroxy-1-methyl-ethyl)-3H-purine, and pharmaceutically acceptable salts thereof.

12. A compound of claim 6 selected from the group consisting of 6-amino-3-(3-cyclopentyloxy-4-methoxy-benzyl)-8-isopropyl-3H-purine, and pharmaceutically acceptable salts thereof.

13. A compound of claim 6 selected from the group consisting of 3-(3-cyclopentyloxy-4-methoxy-benzyl)-6-ethylamino-8-(1-hydroxy-1-methyl-ethyl)-3H-purine, and pharmaceutically acceptable salts thereof.

14. A compound of claim 6 selected from the group consisting of 6-amino-3-(3-cyclopentyloxy-4-methoxy-benzyl)-8-(1-hydroxy-1-methyl-ethyl)-3H-purine, and pharmaceutically acceptable salts thereof.

15. A compound of claim 6 selected from the group consisting of 6-ethylamino-3(3-((1RS, 3RS)-3-hydroxycyclopentyloxy)-4-methoxy-benzyl)-8-(1-hydroxy-1-methyl-ethyl)-3H-purine, pharmaceutically acceptable salts thereof and stereoisometric forms thereof.

16. A compound of claim 6 selected from the group consisting of 6-amino-3-(3-((1RS, 3RS)-3-hydroxycyclopentyloxy)-4-methoxy-benzyl)-8-(1-hydroxy-1-methyl-ethyl)-3 H-purine, pharmaceutically acceptable salts thereof and stereoisometric forms thereof.

17. A compound of claim 6 selected from the group consisting of 6-ethylamino-3-(3-((1RS, 3RS)-3-hydroxycyclopentyloxy)-4-methoxy-benzyl)-.8-isopropyl-3H-purine, pharmaceutically acceptable salts thereof and stereoisometric forms thereof.

18. A compound of claim 6 selected from the group consisting of 6-amino-3-(3-((1RS, 3RS)-3-hydroxycyclopentyloxy)-4-methoxy-benzyl)-8-isopropyl-3H-purine, pharmaceutically acceptable salts thereof and stereoisometric forms thereof.

19. A method for treating a patient suffering from a disease state selected from the group consisting of asthma, allergies, inflammation and depression, said method comprising the administration of a compound selected from the group consisting of:
- 6-amino-3-(3 -cyclopentyloxy-4-methoxy-benzyl)-8-isopropyl-3H-purine;
- 3-(3 -cyclopentyloxy-4-methoxy-benzyl)-6-ethylamino-8-(1-hydroxy-1-methyl-ethyl)-3H-purine;
- 6-amino-3-(3-cyclopentyloxy-4-methoxy-benzyl)-8-(1-hydroxy-1-methyl-ethyl)-3H-purine;
- 6-ethylamino-3(3-((1RS, 3RS)-3-hydroxycyclopentyloxy)-4-methoxy-benzyl)-8-(1-hydroxy-1-methyl-ethyl)-3H-purine;
- 6-amino-3-(3-((1RS, 3RS)-3-hydroxycyclopentyloxy)-4-methoxy-benzyl)-8-(1-hydroxy-1-methyl-ethyl)-3H-purine;
- 6-ethylamino-3-(3-((1RS, 3RS)-3-hydroxycyclopentyloxy)-4-methoxy-benzyl)-8-isopropyl-3H-purine;
- 6-amino-3-(3-((1RS, 3RS)-3-hydroxycyclopentyloxy)-4-methoxy-benzyl)-8-isopropyl-3H-purine;
- pharmaceutically acceptable salts thereof; and
- stereoisometric forms thereof.

20. The method of claim 19 wherein said compound is selected from the group consisting of 6-amino-3-(3-cyclopentyloxy-4-methoxy-benzyl)-8-isopropyl-3H-purine, and pharmaceutically acceptable salts thereof.

21. The method of claim 19 wherein said compound is selected from the group consisting of 3-(3-cyclopentyloxy-4-methoxy-benzyl)-6-ethylamino-8-(1-hydroxy-1-methyl-ethyl)-3H-purine, and pharmaceutically acceptable salts thereof.

22. The method of claim 19 wherein said compound is selected from the group consisting of 6-amino-3-(3-cyclopentyloxy-4-methoxy-benzyl)-8-(1-hydroxy-1-methyl-ethyl)-3H-purine, and pharmaceutically acceptable salts thereof.

23. The method of claim 19 wherein said compound is selected from the group consisting of 6-ethylamino-3(3-((1RS, 3RS)-3-hydroxycyclopentyloxy)-4-methoxy-benzyl)-8-(1-hydroxy-1-methyl-ethyl)-3H-purine, pharmaceutically acceptable salts thereof and stereoisometric forms thereof.

24. The method of claim 19 wherein said compound is selected from the group consisting of 6-amino-3-(3-((1RS, 3RS)-3-hydroxycyclopentyloxy)-4-methoxy-benzyl)-8-(1-hydroxy-1-methyl-ethyl)-3H-purine, pharmaceutically acceptable salts thereof and stereoisometric forms thereof.

25. The method of claim 19 wherein said compound is selected from the group consisting of 6-ethylamino-3-(3-((1RS, 3RS)-3-hydroxycyclopentyloxy)-4-methoxy-benzyl)-8-isopropyl-3H-purine, pharmaceutically acceptable salts thereof and stereoisometlic forms thereof.

26. The method of claim 19 wherein said compound is selected from the group consisting of 6-amino-3-(3-((1RS, 3RS)-3-hydroxycyclopentyloxy)-4-methoxy-benzyl)-8-isopropyl-3H-purine, pharmaceutically acceptable salts thereof and stereoisometric forms thereof.

27. The pharmaceutical composition of claim 1 wherein said compound is selected from the group consisting of 6-ethylamino-3-(3-((1RS, 3RS)-3-hydroxycyclopentyloxy)-4-methoxy-benzyl)-8-isopropyl-3H-purine, pharmaceutically acceptable salts thereof and stereoisometric forms thereof.

28. The pharmaceutical composition of claim 27 which is suitable for oral administration.

29. The pharmaceutical composition of claim 27 which is suitable for administration by inhalation.

30. The pharmaceutical composition of claim 27 which is suitable for parenteral administration.

31. The pharmaceutical composition of claim 1 wherein said compound is selected from the group consisting of 6-amino-3-(3-((1RS, 3RS)-3-hydroxycyclopentyloxy)-4-methoxy-benzyl)-8-isopropyl-3H-purine, pharmaceutically acceptable salts thereof and stereoisometric forms thereof.

32. The pharmaceutical composition of claim 31 which is suitable for oral administration.

33. The pharmaceutical composition of claim 31 which is suitable for administration by inhalation.

34. The pharmaceutical composition of claim 31 which is suitable for parenteral administration.

35. The pharmaceutical composition of claim 1 wherein said compound is selected from the group consisting of 6-amino-3-(3-((1RS, 3RS)-3-hydroxycyclopentyloxy)-4-methoxy-benzyl)-8-(1-hydroxy-1-methyl-ethyl)-3H-purine, pharmaceutically acceptable salts thereof and stereoisometric forms thereof.

36. The pharmaceutical composition of claim 35 which is suitable for oral administration.

37. The pharmaceutical composition of claim 11 which is suitable for oral administration.

38. The pharmaceutical composition of claim 11 which is suitable for administration by inhalation.

39. The pharmaceutical composition of claim 11 which is suitable for parenteral administration.

40. The pharmaceutical composition of claim 1 wherein said compound is selected from the group consisting of 6-ethylamino-3(3-((1RS, 3RS)-3-hydroxycyclopentyloxy)-4-methoxy-benzyl)-8-(1-hydroxy-1-methyl-ethyl)-3H-purine, pharmaceutically acceptable salts thereof and stereoisometric forms thereof.

41. The pharmaceutical composition of claim 40 which is suitable for oral administration.

42. The pharmaceutical composition of claim 40 which is suitable for administration by inhalation.

43. The pharmaceutical composition of claim 40 which is suitable for parenteral administration.

44. The pharmaceutical composition of claim 35 which is suitable for administration by inhalation.

45. The pharmaceutical composition of claim 35 which is suitable for parenteral administration.

* * * * *